United States Patent [19]
Vachette et al.

[11] 3,948,635
[45] Apr. 6, 1976

[54] PROCESS FOR SELECTIVE POST-EMERGENCE WEEDING OF CROPS, AND NEW PRODUCTS BY WHICH THE PROCESS CAN BE IMPLEMENTED

[75] Inventors: Christian Vachette, Paris; Pierre Faillet, Sartrouville, both of France

[73] Assignee: Societe SEPPIC, Paris, France

[22] Filed: June 4, 1969

[21] Appl. No.: 830,536

[52] U.S. Cl. .................. 71/92; 71/111; 71/120; 71/127; 71/DIG. 1
[51] Int. Cl.$^2$ ............................................ A01N 9/22
[58] Field of Search ........... 71/92, 120, 111, DIG. 1

[56] References Cited
UNITED STATES PATENTS

| | | | |
|---|---|---|---|
| 3,235,358 | 2/1966 | Soboczenski | 71/88 X |
| 3,551,131 | 12/1970 | Musselman et al. | 71/93 |
| 3,551,134 | 12/1970 | Brenteson | 71/118 |

FOREIGN PATENTS OR APPLICATIONS

| | | | |
|---|---|---|---|
| 982,344 | 3/1965 | United Kingdom | 71/DIG. 1 |

OTHER PUBLICATIONS

McCowan, Agricultural Chemical, Apr. 1968, 23(4), pp. 18–21.

*Primary Examiner*—Glennon H. Hollrah
*Attorney, Agent, or Firm*—Donald R. Johnson; George L. Church; Anthony Potts, Jr.

[57] ABSTRACT

Spray oil compositions for controlling post-emergence weeds comprising a non-phytotoxic paraffinic oil and an herbicide selected from the group consisting of cyclohexyl-3-trimethylene-5,6-uracil; 1-n-butyl-3(3,4-dichlorophenyl)-1-methyl urea; 5-amino-4-chloro-2-phenyl pyridazine-3-one; and 3-methoxycarbonyl amino phenyl-n-(3-methyl phenyl)-carbamate.

6 Claims, No Drawings

PROCESS FOR SELECTIVE POST-EMERGENCE WEEDING OF CROPS, AND NEW PRODUCTS BY WHICH THE PROCESS CAN BE IMPLEMENTED

BACKGROUND OF THE INVENTION

The invention herein described concerns a process for selective post-emergence weeding and the new products by which the process can be implemented.

There are two differing techniques by which the weeding of crops can be effected. The one consists of pre-emergence dissemination of the herbicide, by which is meant its dissemination before the appearance of said crops above the ground, and usually before the emergence of the undesirable vegetation. The other consists of post-emergence dissemination of the herbicide, by which is meant its dissemination after the germination of said crops and their appearance above the ground, and usually after the appearance of the undesirable vegetation. Obviously the action of the herbicide is quite different in the two cases, and it is self-evident that in most cases it will be necessary to use differing herbicides for the two differing situations. Furthermore, post-emergence weeding calls for a special selection of the herbicide, the choice depending on the crop to be treated and also on the undesirable vegetation to be destroyed. Finally, the stage of development of the crop that is suitable for weeding by means of a given herbicide can have considerable bearing on the results of such treatment.

Consequently, the suitable implementation of post-emergence weeding will require the use of herbicides that are especially active against the undesirable vegetation and are absolutely harmless to the crops being treated.

The invention herein described has for its object the furnishing of means whereby the post-emergence weeding of crops can be carried out. It concerns both a process for carrying out the weeding and certain products used to implement this process.

It has already been established:
1. That certain herbicides possess little effectiveness for use in post-emergence weeding;
2. That certain other herbicides which are ineffective or useless for post-emergence weeding can be effectively used for the post-emergence weeding of crops by the addition to these herbicides of a certain quantity of non-phytotoxic oil.

SUMMARY OF THE INVENTION

The invention herein described thus concerns a post-emergence weeding process for crops, characterized by the fact that a mixture is used which contains a herbicide known to be ineffective or only slightly effective in post-emergence weeding and a non-phytotoxic oil. The non-phytotoxic oil that is used in connection with the invention herein described is a natural oil, essentially paraffinic and containing no more than 10% sulfonatable products.

The invention herein described also has to do with products, mixtures containing a herbicide noted for its ineffectiveness or weak effectiveness in post-emergence weeding and a non-phytotoxic oil, for post-emergence use to implement the process which is the concern of the invention.

DESCRIPTION OF THE INVENTION

The herbicides that have the most particular application to the process covered by the invention are:

Cyclohexyl 3-trimethylene 5,6-uracil (otherwise known as lenacil)

1-n-butyl 3(3,4-dichlorophenyl)-1-methylurea (otherwise known as neburon) which are products known for their inactivity in a post-emergence situation and to which the addition of the oil will confer upon them certain properties of herbicides for post-emergence use:

5-amino-4-chloro-2-phenylpyridazine-3-one (otherwise known as PCA)

3-methoxycarbonylaminophenyl-N-(3'-methylphenyl)-carbamate (otherwise known as phenmedipham)

which are products known to possess a certain herbicidal activity in the post-emergence situation but to which the addition of oil according to the terms of the invention confers upon them a much greater activity.

Other herbicides of the uracil or urea or carbamate type are also usable under the terms of the invention.

The oils usable under the terms of the invention are non-phytotoxic oils of a paraffinic nature and contain no more than 10% of sulfonatable products; of these oils, the ones preferred are certain mineral oil extracts meeting the requirements specified above and having an Engler viscosity at 20°C in the order of 3–10.

It has been established that the effectiveness of a weeding agent, which constitutes a mixture of a herbicide and an oil, increases progressively, all other things being equal, as the quantity of oil used (in liters per hectare) is increased, until it reaches an optimum value, this value varying with respect to the herbicide used in the weeding agent and with respect to the crop being treated. After this optimum point has been reached, the effectiveness of the weeding agent remains constant. It is recommended, however, that the quantity of oil should not be increased beyond about 20–25 liters per hectare, since this would lead to the growth of a certain number of various parasitic phenomena, and in particular to a risk of partial deterioration of the crop itself.

The herbicide-oil mixtures covered by the invention may contain various additives, as for example certain emulsifiers, if one wishes to use said mixtures in the form of an aqueous emulsion.

Although it is true that the process covered by the invention applies to a very general level of usage, the applicant for the patent has also discovered that in many cases it is important to make a proper choice of the herbicide-oil mixture for use in connection with a given crop to be treated and in dependence on the stage of development of that crop. This is why the examples given above, intended as illustrations of the process covered by the invention must also be considered specifically as particular applications to the various crops under consideration.

EXAMPLES a. Treatment of Beet Crops

For the post-emergence weeding of sugar beets and mangel-wurzels, the preferred weeding agent to use consists of at least one herbicide chosen from the group of PCA, phenmedipham, and lenacil plus a non-phytotoxic oil. The quantity of herbicide to use is in the range of 0.5–5 kg/hectare and the quantity of oil is in the range of 2–20 liters/hectare.

This weeding mixture is applied after emergence, when the beets are at least in the cotyledon stage and bearing two true leaves and when the undesirable vegetation, such as one usually finds in beet fields, bear a few true leaves but have not gone to seed.

It will be noted that the quantities of herbicide used are about the same as or less than the quantities usually recommended for the herbicide under consideration. In cases where the herbicide has not normally been used until now in post-emergence weeding, the herbicide content will be based on the figures prescribed for the pre-emergence weeding of these same crops.

Thus, lenacil will preferably be used for a range of content between 0.4 and 1.2 kg/hectare; if 0.6 kg of lenacil is used per hectare, its effectiveness will be excellent, provided one uses at the same time about 5–10 liters of oil per hectare. It will be noted that without the addition of the oil the action of the lenacil under the same conditions is very weak.

Similarly, PCA and phenmedipham will preferably be used in a range of content between 0.5 and 5 kg per hectare; if 3.2 kg of PCA is used per hectare, excellent effectiveness will be attained when at the same time one uses 5–10 liters of oil per hectare; if 0.5 kg of phenmedipham is used per hectare, good effectiveness is obtained with a simultaneous use of 5–10 liters of oil per hectare.

EXAMPLE 1

The following tests, which are not of a limiting nature, illustrate the present application of the invention; these tests involve the selective weeding of sugar beets and mangel-wurzels, the treatment being applied after emergence when the beets had reached and passed the cotyledon stage, with two true leaves, and when the undesirable vegetation was still "young" and had some true leaves. At the time of treatment, it was determined that the fields were overrun with 50–100% self-sowen weeds, common to the locale, among which the most notable representatives were: goosefoot (*Chenopodium album*), knot bindweed (*Polygonum convolvulus*), charlock (*Sinapis arvensis*), jointed charlock (*Raphanus raphanistrum*), cleavers (*Galium aparine*), fumitory (*Fumaria officinales*). This list in no way limits the possibilities.

The results of these tests are to be found in the following tables:

TESTS OF HERBICIDE EFFECTIVENESS. AVERAGE OF OBSERVED RESULTS FOR EACH HERBICIDE

| Products and Concentrations in kg or l/ha | | % Effectiveness on Self-Sown Weeds | % Phytotoxicity to crops |
|---|---|---|---|
| lenacil | 0.6 alone | traces | 0 |
| lenacil | 0.6 + oil 7.5 | 90% | 0 |
| lenacil | 0.8 alone | 0.5% | 0 |
| lenacil | 0.8 + oil 7.5 | 100% | traces |
| lenacil | 1.2 alone | 10% | 10% |
| lenacil | 1.2 + oil 7.5 | 100% | 20% |
| P.C.A. | 1.6 alone | 10% | 0 |
| P.C.A. | 1.6 + oil 7.5 | 50% | 0 |
| P.C.A. | 3.2 alone | 10% | 0 |
| P.C.A. | 3.2 + oil 7.5 | 80% | 0 |
| P.C.A | 4.8 alone | 50% | 0 |
| P.C.A. | 4.8 + oil 7.5 | 90% | traces |
| phenmedipham | 1.2 alone | 50% | 0 |
| phenmedipham | 1.2 + oil 7.5 | 100% | 0 |
| phenmedipham | 2.4 alone | 80% | 0 |
| phenmedipham | 2.4 + oil 7.5 | 100% | 0 |
| phenmedipham | 4.8 alone | 100% | 0 |
| phenmedipham | 4.8 + oil 7.5 | 100% | 0 |
| parrafinic oil | alone 7.5 | 0 | 0 |
| lenacil | 0.6 alone | traces | 0 |
| lenacil | 0.6 + oil 5 | 80% | 0 |
| lenacil | 0.6 + oil 10 | 90% | 0 |
| lenacil | 0.8 alone | 10% | 0 |
| lenacil | 0.8 + oil 5 | 90% | 0 |
| lenacil | 0.8 + oil 10 | 90% | traces |
| lenacil | 1.2 alone | 10% | 10% |
| lenacil | 1.2 + oil 5 | 80% | 10% |
| lenacil | 1.2 + oil 10 | 90% | 50% |
| P.C.A. | 1.6 alone | 10% | 0 |
| P.C.A. | 1.6 + oil 5 | 80% | 0 |
| P.C.A. | 1.6 + oil 10 | 100% | traces |
| P.C.A. | 3.2 alone | 80% | 0 |
| P.C.A. | 3.2 + oil 5 | 95% | 0 |
| P.C.A. | 3.2 + oil 10 | 95% | traces |
| P.C.A. | 4.8 alone | 85% | 0 |
| P.C.A. | 4.8 + oil 5 | 100% | 10% |
| P.C.A. | 4.8 + oil 10 | 100% | 20% |
| phenmedipham | 0.5 alone | 50% | 0 |
| phenmedipham | 0.5 + oil 5 | 80% | 0 |
| phenmedipham | 0.5 + oil 10 | 80% | 0 |
| phenmedipham | 2.4 alone | 95% | 0 |
| phenmedipham | 2.4 + oil 5 | 100% | 0 |
| phenmedipham | 2.4 + oil 10 | 100% | 0 |
| phenmedipham | 4.8 alone | 100% | 0 |
| phenmedipham | 4.8 + oil 5 | 100% | 0 |
| phenmedipham | 4.8 + oil 10 | 100% | 0 |
| paraffinic oil | alone 5 | 0 | 0 |
| paraffinic oil | alone 10 | 0 | 0 |
| paraffinic oil | alone 15 | 0 | 0 |
| paraffinic oil | alone 20 | 0 | 0 |
| paraffinic oil | alone 40 | 0 | 0 |

EXAMPLE 2
Crop Yields. For Post-Emergence Applications to Self-Sown Weeds and Crops

| Active Ingredients kg/ha | Tonnage of Roots/ha | Saccharide Concentration | Tonnage of Roots/ha | Saccharide Concentration |
| --- | --- | --- | --- | --- |
| lenacil 0.6 + paraffinic oil 5 l | 56.10 | 16.5% | 38.3 | 17.3% |
| lenacil 0.8 + paraffinic oil 5 l | 56.60 | 16.5% | 36.6 | 17.0% |
| lenacil 0.6 + paraffinic oil 10 l | 55.0 | 16.3% | 35.6 | 17.1% |
| lenacil 0.8 + paraffinic oil 10 l | 54.50 | 16.7% | 36.0 | 17.6% |
| lenacil 0.6 alone | 47.2 | 16.9% | 27.6 | 16.8% |
| lenacil 0.8 alone | 50.8 | 16.7% | 29.8 | 17.0% |
| control crops, not treated, mechanically weeded | 52.6 | 16.8% | 34.65 | 16.5% |

The use of lenacil alone for post-emergence application to the combination of self-sown weeds and beets did not cause sufficient destruction of the undesirable vegetation, thus causing a notable loss of yield: the weeds were running competition with the crop.

By contrast, the addition of the natural paraffinic oil at a normal rate for use of lenacil (0.8 kg/hectare) or at a lower rate than normal, allows an increase of 5–10% of the quantitative yield (in tons of beets per hectare) without reducing the saccharide content, whose percentages are usually constant for treated and untreated plots of ground; consequently, this treatment increases the qualitative yield (tons of sugar per hectare).

b. Treatment of Tomato Crops

For the post-emergence weeding of tomato plants, it is preferable to use a weeding agent composed of a mixture of lenacil with non-phytotoxic oil.

Usable quantities of lenacil run in the order of 0.4–2 kg per hectare and the quantities of oil must be in the range of 2–15 liters per hectare. With respect to the invention, the lenacil will be premixed with the oil.

Thus, in the example given below—which is not intended to limit the area of application—some fields of tomatoes were treated with mixtures containing lenacil and oil. The respective quantities of lenacil and oil were such that the three plots of ground treated received 5 liters of oil per hectare and 0.6–1.2 and 1.8 kg, respectively, of lenacil per hectare. The following results were obtained:

EXAMPLE 3

| Quantity of lenacil used | % Effectiveness | % Phytotoxicity |
| --- | --- | --- |
| 0.6 | 95 | 0 |
| 1.2 | 100 | 0 |
| 1.8 | 100 | 10 |

Thus, by the use of 1.2 kg of lenacil per hectare, this weeding agent being mixed with a quantity of oil corresponding to 5 liters of oil per hectare, it was possible to totally suppress the undesirable vegetation without damaging the tomato plants. The final yield demonstrated that the quantity of tomatoes picked from the treated plots of ground was clearly more than that picked from plots of ground that were not treated nor mechanically weeded and at least equal to the amount picked from ground not treated but given three hoeings.

c. Treatment of Corn* Crops

*[I am using "corn" in the American sense of the word. Tr.]

For the post-emergence weeding of corn crops, it is preferable to use a weeding agent consisting of a mixture of neburon and non-phytotoxic oil.

The quantities of neburon that can be used are in the order of 0.5–3 kg per hectare, and the quantities of oil must be in the range of 5–20 liters per hectare. With reference to the invention, the neburon is premixed with the oil.

Thus, in the following example—not intended to limit the application—some fields of corn were treated with mixtures containing neburon and oil.

The respective quantities of neburon and oil were such that the three plots of ground treated received 10 liters of oil and 0.5, 1, 2 and 3 kg, respectively, of neburon per hectare.

The following results were obtained:

EXAMPLE 4

| Amount of neburon used per hectare | % of Effectiveness Gramineae | Orache | % of Phytotoxicity |
| --- | --- | --- | --- |
| 0.5 kg | 75 | 85 | 0 |
| 1 kg | 95 | 100 | 0 |
| 2 kg | 100 | 100 | 0 |
| 3 kg | 100 | 100 | 0 |

Thus, by the use of 1–2 kg of neburon per hectare, this weeding agent being mixed with a quantity of oil corresponding to 10 liters of oil per hectare, it was possible to totally suppress the more obnoxious weeds without damaging the corn.

It should be noted further that these mixtures can exercise a certain phytotoxic action on the corn crops when they are sprayed directly onto the leaves of the corn plants. Consequently, it would be desirable during treatment to use every known means of avoiding the direct spraying of said weeding agent onto the corn leaves.

d. Treatment of Spinach Crops

For the post-emergence weeding of spinach crops, it is preferable to use a weeding agent consisting of a mixture of lenacil and non-phytotoxic oil.

The concentrations of lenacil can vary from 0.4 to 1.6 kg/hectare and the oil concentrations from 5 to 15 liters/hectare.

The results of various tests are as follows:

The tests were carried out on autumn crops of spinach at the stage of 6–8 true leaves. The crop was clean or devoid of weeds at the time of treatment: no reckoning was made of the effectiveness of the herbicide on the self-sown vegetation. In other words, this was a test of phytotoxicity to the crop.

Furthermore, the test took place over soil that permitted a high amount of seepage of the finer material (loam, sand).

The experimentation demonstrated a good selectivity of the herbicide mixture even in high-seepage soil, which is the type of soil generally not recommended for pre-emergence treatment with lenacil alone.

Plots of land 25 m$^2$ in area were treated once only:

EXAMPLE 5

|  |  | % Phytotoxicity to the Crop |
|---|---|---|
| lenacil | 0.4 alone | 0 |
| lenacil | 0.4 + 5 l oil | 0 |
| lenacil | 0.6 alone | 0 |
| lenacil | 0.6 + 5 l oil | 0 |
| lenacil | 0.8 alone | 0 |
| lenacil | 0.8 + 5 l oil | 0 |
| lenacil | 1.6 alone | 0 |
| lenacil | 1.6 + 5 l oil | 0 |
| untreated control plot |  | 0 |

Treatment carried out on autumn crops of spinach having 4 true leaves and with the self-sown vegetation just beginning to emerge. Plots of land 10 m$^2$ in area were treated once only:

EXAMPLE 6

|  |  | % of Effectiveness on Weeds | % of Phytotoxicity to Crop |
|---|---|---|---|
| lenacil | 0.4 alone | 20% | 0 |
| lenacil | 0.4 + 10 l oil | 70% | 0 |
| lenacil | 0.6 alone | 30% | 0 |
| lenacil | 0.6 + 10 l oil | 80% | 0 |
| lenacil | 0.8 alone | 50% | 0 |
| lenacil | 0.8 + 10 l oil | 95% | 0 |
| untreated control plot |  | 0 | 0 |

Tests carried out on winter crops of spinach having 4 true leaves and self-sown vegetation with 2 true leaves (excepting chickweed, which had grown 4–5 cm). Plots of ground 10 m$^2$ in area, 3 repetitions:

EXAMPLE 7

|  |  | % of Effectiveness on Weeds | % of Phytotoxicity to Crop |
|---|---|---|---|
| lenacil | 0.4 alone | 70% | 0 |
| lenacil | 0.4 + 5 l oil | 100% | 0 |
| lenacil | 0.4 + 10 l oil | 100% | 0 |
| lenacil | 0.6 alone | 80% | 0 |
| lenacil | 0.6 + 5 l oil | 100% | 0 |
| lenacil | 0.6 + 10 l oil | 100% | 0 |
| lenacil | 0.8 alone | 100% | 0 |
| lenacil | 0.8 + 5 l oil | 85% | 0 |
| lenacil | 0.8 + 10 l oil | 100% | 0 |
| lenacil | 1.6 + 10 l oil | 100% | 20% |
| untreated control crops: especially overrun (20%) with chickweed and dog's mercury |  | 0 | 0 |

The results of the tests described above are as follows:

1. They confirmed the foliar effectiveness against young weed plants treated with lenacil to which a paraffinic oil had been added, provided that the spraying was carried out on weeds shortly after germination, when they possessed 2 cotyledons or 2–4 true leaves or more, depending on the species.

2. They confirmed that a foliar treatment with a lenacil-paraffinic oil mixture depends very little for its effectiveness on the nature of the soil (seepage soil, for example).

3. They confirmed that a reduction of the lenacil content was possible with the addition of the paraffinic oil, provided that climatic conditions are favorable at the time of treatment: notably, during mild, wet weather. This reduction of the lenacil content would seem to be practicable down to 0.4 kg per hectare, which means that it reduces the production costs per hectare.

This possible reduction of the lenacil content brings with it a reduction of the risk of phytotoxicity to the crops, and a continuance of the reducing action. In fact, an early post-emergence treatment of the self-sowing vegetation has no effect on the continuance of this reduction of the amount of lenacil applied to the soil. This could have some significance in the case of spring crops of spinach with a short vegetative cycle (about 60 days), which is usually followed, after its harvest, by another crop, one that is often more sensitive (lettuce, for example), or that could not withstand the residual effects of lenacil on the soil.

4. They demonstrated the high selectivity of lenacil with respect to spinach in the process of growth (with at least 2–4 true leaves) when the herbicide is applied after emergence of the crop and as part of a mixture with a paraffinic oil.

e. Treatment of Woody Plants

For the weeding of woody plants vines and fruit trees, for example) it is preferable to use a weeding agent consisting of a mixture of neburon and non-phytotoxic oil.

The amounts of neburon to be used are in the order of 0.5–3 kg/hectare, and the amounts of oil are in the range of 5 to 20 liters/hectare.

The table below gives the results obtained, averaged over several tests:

EXAMPLE 8

| Amounts Used | | % of Effectiveness Against Weeds (15 Days After Application) | | % of Phytotoxicity (1 Year After Application) to: | |
|---|---|---|---|---|---|
| Herbicide kg/ha | Oil l/ha | Gramineae | Dicotylenes | Grapevines | Fruit Trees* |
| 0.5 | 5 | 65 | 75 | 0 | 0 |
| 1 | 5 | 85 | 95 | 0 | 0 |
| 2 | 5 | 95 | 100 | 0 | 0 |
| 3 | 5 | 100 | 100 | 0 | 0 |
| 0.5 | 10 | 75 | 85 | 0 | 0 |
| 1 | 10 | 95 | 100 | 0 | 0 |
| 2 | 10 | 100 | 100 | 0 | 0 |
| 3 | 10 | 100 | 100 | 0 | 0 |
| 0.5 | 15 | 90 | 95 | 0 | 0 |
| 1 | 15 | 90 | 95 | 0 | 0 |
| 2 | 15 | 90 | 95 | 0 | 0 |
| 3 | 15 | 90 | 95 | 0 | 0 |

*The fruit trees include: apple, pear, apricot, cherry, peach, and plumb.

For this treatment, given the possible phytotoxic action of the mixture on the leaves of the woody plants, care was taken to spray the weeding agent only on the undesirable vegetation.

The greater part of the results given above were obtained using oils of mineral origin containing 6% sulfonatable products; some similar results were obtained in each category by using oils containing 2.4% and as high as 10% sulfonatable products; beyond this latter percentage, the results are not as good.

We claim

1. A process for post-emergence weeding of crops comprising the use of a mixture containing one herbicide selected from the following group: cyclohexyl-3-trimethylene 5,6-uracil, 1-butyl-3(3,4-dichlorophenyl)-1-methyl-urea, 5-amino-4-chloro-2-phenyl-pyridazine-3-one, and 3-methoxycarbonylaminophenyl-N-(3'-methylphenyl)-carbamate; and a non-phytotoxic oil wherein said oil is essentially paraffinic and contains no more than 10% sulfonatable products and is used in concentrations of 2–25 liters/hectare, and wherein said uracil is used in concentrations of 0.4–2 kg/hectare; said phenylpyridazine is used in concentrations of 1.2–4.8 kg/hectare; said carbamate is used in concentrations of 0.5–5 kg/hectare.

2. Process according to claim 1 wherein said crop is beets and the herbicide is said uracil, or said phenylpyridazine or said carbamate and the treatment taking place when the beets have reached or passed the cotyledon stage with 2 true leaves and when the undesirable vegetation has not yet passed the young-plant stage and has some true leaves, the amount of the mixture used is in the range from 0.5 to 5 kg of herbicide per hectare and from 2 to 20 liters of non-phytotoxic oil per hectare.

3. Process according to claim 1 wherein said crop is tomatoes and the herbicide is said uracil and the amount of mixture used is between 0.4 and 2.0 kg of uracil per hectare and from 2 to 15 liters of oil per hectare.

4. Process according to claim 1 wherein said crop is corn and the herbicide is said methylurea and the amount of mixture used is between 0.5 and 3 kg of methylurea per hectare and from 5 to 20 liters of oil per hectare, said mixture being applied in such a manner that spray droplets do not touch the leaves of the corn plants.

5. Process according to claim 1 wherein said crop is spinach and the herbicide is said uracil and the amount of mixture used is between 0.4 and 2 kg of uracil per hectare and from 2 to 15 liters of oil per hectare.

6. Process according to claim 1 wherein said crop is woody plants and the herbicide is said methylurea and the amount of mixture used is between 0.5 and 3 kg of methylurea per hectare and from 5 to 20 liters of oil per hectare, said mixture being applied in such a manner that the spray droplets touch only the undesirable vegetation and not the leaves of said woody plants.

* * * * *